US00PP33173P2

(12) United States Plant Patent
Moerman

(10) Patent No.: US PP33,173 P2
(45) Date of Patent: Jun. 15, 2021

(54) ***LAVANDULA* PLANT NAMED 'AGRI811'**

(50) Latin Name: *Lavandula stoechas*
Varietal Denomination: AGRI811

(71) Applicant: Marcel Moerman, De Lier (NL)

(72) Inventor: Marcel Moerman, De Lier (NL)

(73) Assignee: AGRIVERCO GENETICS B.V., De Lier (NL)

( * ) Notice: Subject to any disclaimer, the term of this patent is extended or adjusted under 35 U.S.C. 154(b) by 0 days.

(21) Appl. No.: 16/974,061

(22) Filed: Sep. 18, 2020

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 6/502; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Lavandula* plant named 'AGRI811', characterized by its upright to broadly spreading plant habit; freely branching growth habit; freely flowering habit; relatively large dark purple-colored flowers and lighter purple-colored terminal flower bracts positioned on strong and erect peduncles; long flowering period; and good garden performance.

1 Drawing Sheet

Botanical designation: *Lavandula stoechas.*
Cultivar denomination: 'AGRI811'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Lavandula* plant, botanically known as *Lavandula stoechas*, commonly referred to as Lavender and hereinafter referred to by the name 'AGRI811'.

The new *Lavandula* plant is a product of a planned breeding program conducted by the Inventor in De Lier, The Netherlands. The objective of the breeding program was to develop new unique *Lavandula* plants with long flowering period and attractive plant form and flower coloration.

The new *Lavandula* plant originated from a cross-pollination in July, 2015 of a proprietary selection of *Lavandula stoechas* identified as code designation agri 279, not patented, as the female, or seed, parent with a proprietary selection of *Lavandula stoechas* identified as code designation agri 425, not patented, as the male, or pollen, parent. The new *Lavandula* plant was discovered and selected by the Inventor as a single flowering plant within the progeny of the stated cross-pollination in a controlled environment in De Lier, The Netherlands in April, 2016.

Asexual reproduction of the new *Lavandula* plant by terminal cuttings in a controlled greenhouse environment in De Lier, The Netherlands since May, 2016 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'AGRI811' as a new and distinct *Lavandula* plant:

1. Upright to broadly spreading plant habit.
2. Freely branching growth habit.
3. Freely flowering habit.
4. Relatively large dark purple-colored flowers and lighter purple-colored terminal flower bracts positioned on strong and erect peduncles.
5. Long flowering period.
6. Good garden performance.

Plants of the new *Lavandula* differ primarily from plants of the female parent selection primarily in leaf size and color as plants of the new *Lavandula* have broader and more greyed-colored leaves than plants of the female parent selection.

Plants of the new *Lavandula* differ primarily from plants of the male parent selection primarily in growth habit as plants of the new *Lavandula* are more compact than plants of the male parent selection. In addition, plants of the new

*Lavandula* have purple-colored terminal flower bracts whereas plants of the male parent selection have lilac-colored terminal flower bracts.

Plants of the new *Lavandula* can be compared to plants of the *Lavandula stoechas* 'Dark Knight', not patented. In side-by-side comparisons, plants of the new *Lavandula* differ primarily from plants of 'Dark Knight' in the following characteristics:

1. Plants of the new *Lavandula* are broader and more greyed-colored leaves than plants of 'Dark Knight'. 2. Plants of the new *Lavandula* have larger flowers than plants of 'Dark Knight'. 3. Plants of the new *Lavandula* have purple-colored terminal flower bracts whereas plants of 'Dark Knight' have lilac-colored terminal flower bracts.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type. Colors in the photograph may differ slightly from the color values cited in the detailed botanical description which accurately describe the colors of the new *Lavandula* plant. The photograph is a side perspective view of a typical flowering plant of 'AGRI811' grown in a container.

DETAILED BOTANICAL DESCRIPTION

Plants used in the aforementioned photograph and following detailed description were grown in 12-cm containers during the spring in an outdoor nursery in Luz De Tarvira, Portugal and under cultural practices typical of commercial *Lavandula* production. Plants were pinched four and eight weeks after planting and were six months old when the photograph and description were taken. During the production of the plants, day temperatures ranged from 18° C. to 20° C. and night temperatures ranged from 8° C. to 10° C. In the following description, color references are made to The Royal Horticultural Society Colour Chart, 2015 Edition, except where general terms of ordinary dictionary significance are used.

Botanical classification: *Lavandula stoechas* 'AGRI811'.

Parentage:

*Female, or seed, parent*.—Proprietary selection of *Lavandula stoechas* identified as code designation agri 279, not patented.

*Male, or pollen, parent*.—Proprietary selection of *Lavandula stoechas* identified as code designation agri 425, not patented.

Propagation:

*Type*.—Terminal vegetative cuttings.

*Time to initiate roots, summer*.—About two weeks at temperatures about 18° C.

*Time to initiate roots, winter*.—About three weeks at temperatures about 18° C.

*Time to produce a rooted young plant, summer*.—About two weeks at temperatures about 18° C.

*Time to produce a rooted young plant, winter*.—About four weeks at temperatures about 18° C.

*Root description*.—Medium in thickness, fleshy; typically creamy white in color, actual color of the roots is dependent on substrate composition, water quality, fertilizer type and formulation.

*Rooting habit*.—Low branching; sparse.

Plant description:

*Plant and growth habit*.—Herbaceous perennial; upright and broadly spreading plant habit; broadly obovate in overall plant shape; freely branching habit; moderately vigorous growth habit; moderate growth rate; flowers arranged in verticillasters on crowded spikes with showy terminal flower bracts.

*Plant height, soil level to top of foliar plane*.—About 23.5 cm.

*Plant height, soil level to top of floral plane*.—About 26.3 cm.

*Plant width*.—About 29.1 cm.

*Lateral branch description*.—Quantity per plant: About nine primary lateral branches each with about four to nine secondary lateral branches developing per plant. Length: About 10 cm. Diameter: About 2 mm. Internode length: About 2 cm. Strength: Moderately strong. Aspect: Primary lateral branches, upright to about 70° from vertical; secondary lateral branches, about 10° to 35° from primary lateral branch axis. Texture and luster: Densely tomentose; slightly glossy. Color, when developing: Close to 145A. Color, developed: Close to 144B and 145B; with development, close to N199A and N199B.

*Leaf description*.—Arrangement: Opposite, simple; sessile. Length: About 3.8 cm. Width: About 8mm. Shape: Narrowly oblanceolate. Apex: Broadly acute. Base: Cuneate. Margin: Entire; slightly revolute; not lobed. Texture and luster, upper surface: Densely tomentose; not rugose; matte. Texture and luster, lower surface: Moderately to densely tomentose; slightly rugose; matte. Fragrance: Strongly aromatic, pungent. Venation pattern: Pinnate. Color: Developing leaves, upper surface: Close to 137D. Developing leaves, lower surface: Close to 138B. Fully expanded leaves, upper surface: Close to NN137D; venation, close to NN137D. Fully expanded leaves, lower surface: Close to between 138A and N138B; venation, close to 138A.

Flower description:

*Flower type, arrangement and habit*.—Single salver-form flowers arranged in compact verticillasters on crowded terminal spikes; freely flowering, about 200 flowers developing per inflorescence and about 7,500 flowers developing per plant; flowers with two-lobed upper lip and three-lobed lower lip; flowers face mostly outwardly on the spike; inflorescences with showy terminal flower bracts.

*Natural flowering season*.—Long flowering period; continuous from late spring into the summer in The Netherlands.

*Flower longevity on the plant*.—Inflorescences last about eight weeks on the plant; flowers not persistent.

*Fragrance*.—None detected.

*Flower buds*.—Length: About 4 mm. Diameter: About 1.25 mm. Shape: Oblong. Texture and luster: Densely tomentose; matte. Color: Close to 145D; distally, close to 146D and at the apex, close to 79D.

*Inflorescence size*.—Height, excluding terminal flower bracts: About 2.8 cm. Height, including terminal flower bracts: About 5 cm. Diameter, at terminal flower bracts: About 3.5 cm. Diameter, below flower bracts: About 1.6 cm.

*Flower size*.—Diameter: About 5 mm by 5 mm. Depth (height): About 9 mm. Throat diameter: About 1.5 mm. Tube length: About 5 mm. Tube diameter: About 1.25 mm.

*Petals*.—Quantity and arrangement: Upper lip, two-lobed and lower lip, three-lobed. Length, upper lip: About 1.1 cm. Length, lower lip: About 8 mm. Width, upper lip: About 2 mm. Width, lower lip: About 2 mm. Shape: Roughly spatulate; lower 70% fused into a tube. Apex: Obtuse, rounded. Margin: Entire; not undulate. Texture and luster, upper surface: Smooth, glabrous; velvety; matte. Texture and luster, lower surface: Smooth, glabrous; moderately velvety; matte. Texture, throat and tube: Smooth, glabrous; slightly velvety; matte. Color: When opening and fully opened, upper surface: Close to 83A; venation, close to 83A; color becoming closer to N186B with development. When opening and fully opened, lower surface: Close to 83B; venation, close to 83B; color becoming closer to N186B with development. Throat: Close to 83B; venation, close to 83B. Tube: Close to 83D fading proximally to close to N155A; venation, close to 83D fading proximally to close to N155A.

*Terminal flower bracts*.—Quantity and arrangement: About four positioned at inflorescence apex. Length: About 3.1 cm. Width: About 9.5 mm. Shape: Narrowly oblanceolate to narrowly obovate. Apex: Acute. Base: Narrowly cuneate. Margin: Entire; moderately undulate. Texture and luster, upper and lower surfaces: Sparsely tomentose; matte. Color, upper surface: Close to N81B and N82A; midvein, close to N186A. Color, lower surface: Close to N81B and N82A; midvein, close to 79B.

*Basal flower bracts*.—Quantity and arrangement: Each group of seven flowers is subtended by a single basal flower bract. Length: About 6 mm. Width: About 8 mm. Shape: Broadly rhomboidal. Apex: Broadly and abruptly acute. Base: Cuneate. Margin: Entire. Texture and luster, upper surface: Mostly glabrous with pubescence along margins; slightly glossy. Texture and luster, lower surface: Sparsely tomentose; matte. Color, upper surface: Close to N79C; venation, close to 146A. Color, lower surface: Close to N79A and N79B; venation, close to between N186C and N200A.

*Sepals*.—Quantity and arrangement: Five, lower 85% of the sepals are fused into a campanulate tube. Calyx length: About 5.5 mm. Calyx diameter: About 1.5 mm. Length: About 5 mm. Width: About 1 mm. Shape: Lanceolate. Apex: Acute. Margin: Entire. Texture and luster, upper surface: Smooth, glabrous; glossy. Texture and luster, lower surface: Densely pubescent; slightly glossy. Color: When opening and fully opened, upper surface: Close to 145D; venation, close to 143B. When opening and fully opened, lower surface: Proximally, close to 145D; distally, close to 146D; at the apex, close to 79D.

*Peduncles*.—Length: About 4.9 cm. Diameter: About 2 mm. Aspect: Mostly upright. Strength: Strong. Texture and luster: Densely tomentose; matte. Color: Close to 144B and 145B; distally, tinged with close to N186C.

*Reproductive organs*.—Stamens: Quantity per flower: Four. Filament length: About 1 mm. Filament color: Close to N155A. Anther shape: Reniform; dorsifixed. Anther size: About 0.5 mm by 0.5 mm. Anther color: Close to N186A. Pollen amount: Scarce to moderate. Pollen color: Close to 14C. Pistils: Quantity per flower: One. Pistil length: About 4 mm. Stigma shape: Club-shaped. Stigma diameter: About 0.5 mm. Stigma color: Close to N186A. Style length: About 3.5 mm. Style color: Close to N155A. Ovary color: Close to N144D.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be suitable for USDA Hardiness Zones 7 to 10.

It is claimed:

1. A new and distinct *Lavandula* plant named 'AGRI811' as illustrated and described.

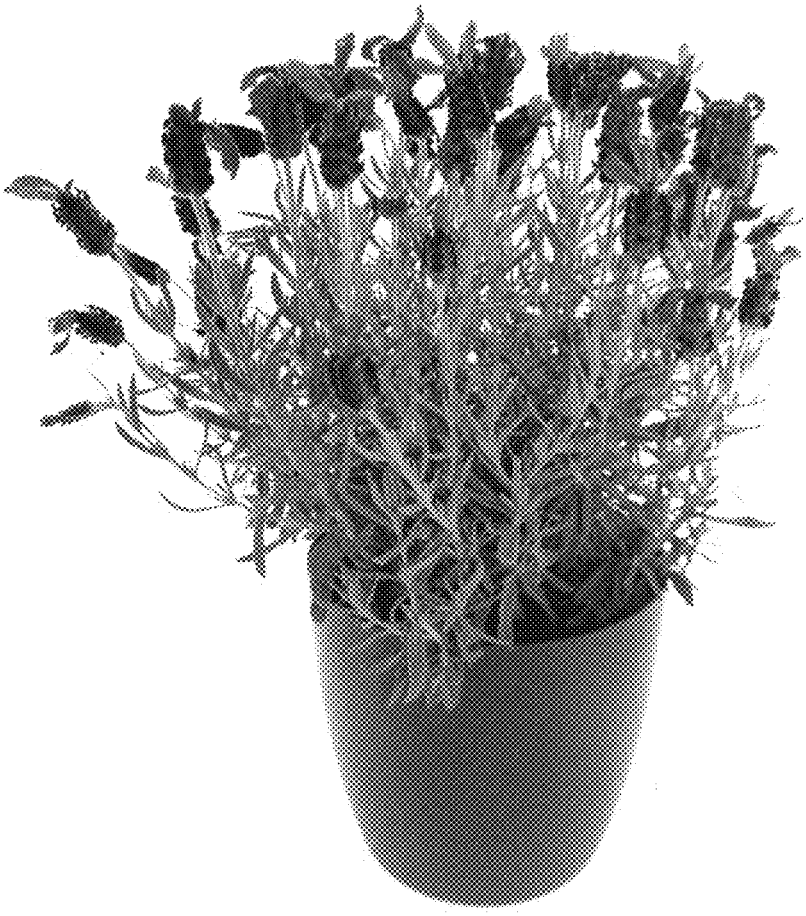

* * * * *